Jan. 1, 1952 J. D. BROWNELL Plant Pat. 1,059
ROSE PLANT
Filed May 9, 1950
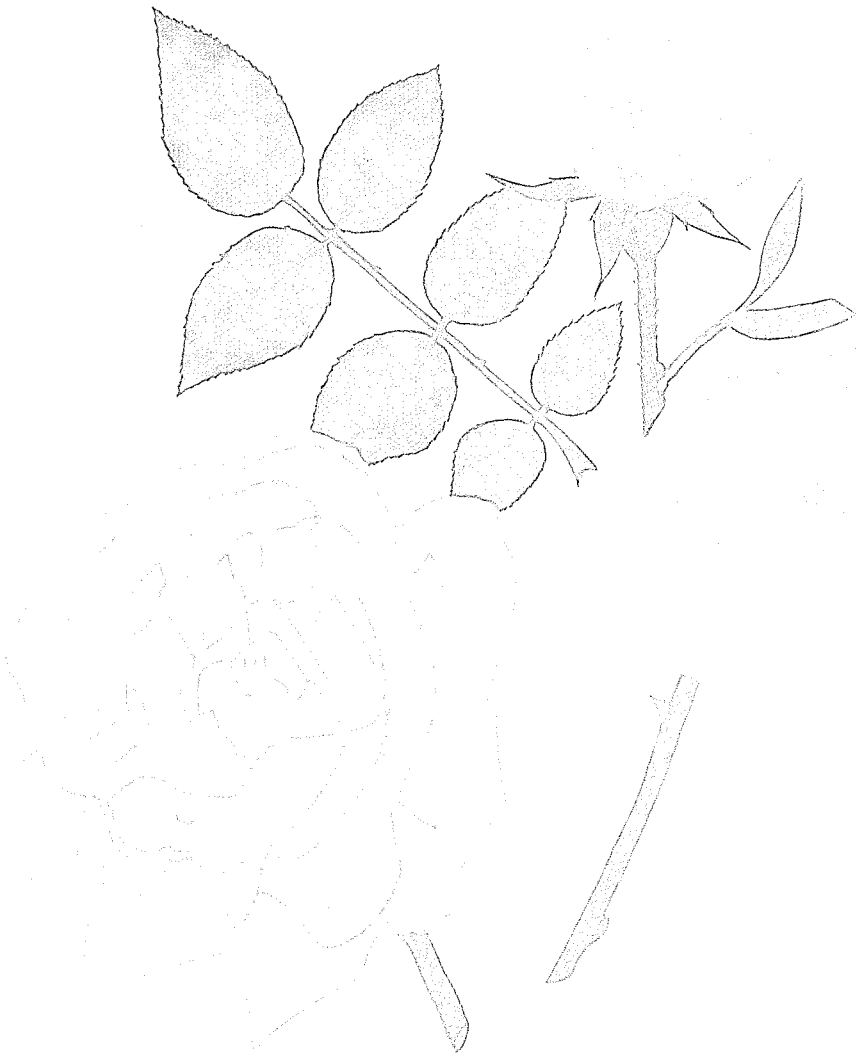
Josephine D. Brownell
INVENTOR.

Patented Jan. 1, 1952

Plant Pat. 1,059

UNITED STATES PATENT OFFICE 1,059

ROSE PLANT

Josephine D. Brownell, Little Compton, R. I.

Application May 9, 1950, Serial No. 160,845

1 Claim. (Cl. 47—61)

My invention relates to roses and especially to a new, original and distinct variety of the class known commercially as "hybrid teas" and is a variant in that class, being a *Rosa wichuraiana* hybrid tea hybrid, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States:

The pink to orange shades (ordinary dictionary definition) of its petals, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers, notably after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by black-spot, under certain definite conditions of exposure, without any cultural control.

In the accompanying drawing forming a part of this specification I have shown my new rose in its natural colors, that is, as near as is possible to do so artificially.

My new rose is otherwise described as follows:

Type: Hybrid tea, *Rosa wichuraiana* hybrid, dwarf to ascending to tall bush, for garden display, cut flower and forcing or growing under glass.

Class: Hybrid tea crossed with *Rosa wichuraiana*, further restricted by originator to include only those varieties that can survive moderately low sub-zero temperatures.

Breeding: This variety was produced and bred by me and under my direction by propagation and cross pollenation.

It came into being as a seedling grown from a seed borne on a plant of "Pink Princess" (Plant Patent 459) and the pollen parent was "Stargold" (Plant Patent 248), both parents having been produced by me and under my direction.

The pollenation that fertilized the seed that grew into my new rose, as well as the two previous pollenations that produced the two parents of my new rose, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 2, 1946.[1] The seed was planted for me and under my direction on December 28, 1946, and the date of the first flower was July 24, 1947.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1947–9 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one and frequently two or three and occasionally more on each stem, in the usual hybrid tea type of cluster. The pedicels and peduncles are medium in diameter and medium in length, erect, stiff, almost smooth, free from large prickles and bristles but with a few very small prickles varying to small hairs. Stems are long, diameter medium to small and notably stiff and rigid.

Quantity of bloom: Free, being cumulative in quantity from year to year as the plant increases in size, flowering through the summer and fall.

Fragrance: Distinctive, pleasing China tea in combination with that of *Rosa wichuraiana*, under favorable environment.

Bud: Neck normal as described, opens well, being little to not at all affected by hot or wet weather or both, as to color and form, except at very high temperatures the color is less intense and the form of the petals is less recurled.

[1] This and other dates herein are approximate.

Before the calyx breaks the size is medium, form notably ovoid, frequently with one or more sepals having foliaceous parts extending beyond the apex of the calyx up to about three quarters of an inch, the number and size of the foliaceous parts being variable and rarely having one or more narrow, pointed, minutely serrate appendages on each side of the sepals, otherwise the sepals are usually normal and regular, tapering to lanceolate at the apex, turning back nearly perpendicular to the pedicel as the bud opens.

Color of the bud as the calyx opens: outside of petals Mandarin Red 17/1, page 17, inside of petals same; color reference to English Horticultural Colour Chart by R. F. Wilson (1941).[1]

Bloom: As the bud opens and the flower develops to maturity the color outside of petals slowly changes toward Mandarin Red 17/2 and Mandarin Red 17/3, page 17.

The flower usually varies in size between four inches and five inches in diameter when fully open, petals average around 45, frequently some smaller petals and petaloids in the center, variable in number.

The flower opens globular, informal, incurled, with late display of stamens and pistils. The petals are variable from obovate to ovate to irregular and frequently with surfaces variously warped and edges especially of the smaller petals frequently notably irregular. Texture is medium to thick and leathery; both sides brilliant with slight veining which is not prominent. The time of opening in favorable conditions is three to five days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

Productive organs:

*Stamens*, quantity variable, medium long, slightly uneven in length.

*Anthers*, nearly Marigold Orange at 11/3, page 11.

*Filaments*, nearly Tangerine Orange at 9/3, Page 9.

*Pistils* are several, slightly uneven in length, averaging about one-half inch long.

*Ovaries* are usually all inclosed.

*Hips* do not develop at Little Compton, Rhode Island.

*Sepals* are persistent and break off easily.

*Plant*

Foliage: Is abundant, of compound leaves of three to five leaflets near the flower, five leaflets lower down the stem and frequently seven leaflets in the middle of the stem and nearer the base. Size of leaflets medium, averaging in size a little larger than half way between the average hybrid tea and the *Rosa wichuraiana* leaflets. As the plants develop in size some of the leaflets develop to twice the size described above. Form of leaflets usually ovate with apex moderately acute, base rounded, in some instances with the circumference on one side of the petiolule out of alignment with the other side by about one-sixteenth of an inch or less, margins with slightly irregular small pointed serrations, petiolules short.

[1] Color references to same unless otherwise indicated.

The leaflets average in width about one-half to two-thirds of their length.

Color of leaflets on the upper surface is slightly variable from Scheeles Green at 860, page 175, irreguluarly shaded with Spinach Green at o960/1, page 187, with reverse side nearly Asphodel Green frequently overlaid with trace of Dahlia Carmine, the last two color references are to Robert Ridgway Color Standards.

The rachises are medium, moderately narrow to slender, upper side smooth except some very short hairs on edge. Under side moderately smooth, usually 3 to 5 short prickles.

Stipules are medium to long, averaging about three-quarters of an inch long, with sharp points, the upper edges of which normally form an angle of about 90 degrees.

Habit, dwarf, becoming bushy and taller; upright, compact, more cumulative in growth from year to year than the normal hybrid tea rose plant, by stems from the base and by rebranching and growth and enlargement and extension of the stems from the base. The growth is moderately free at first, developing more rapidly after one or two years under favorable vegetative opportunity.

Color of mature stems is Scheeles Green at 860/3, page 175, shading variously lighter and also occasionally with slight overlay of Spinel Red at oo23/1, page 189, variable in intensity, usually more pronounced on the sunny side.

Prickles, several, frequently two to four between leaves, averaging in length about one-quarter inch, shading from Crimson at 22, page 22, to lighter at the base, turning lighter throughout and later to nearly colorless. Hairs few on upper portions of stems.

Winter resistance: A notable characteristic of this new rose is the resistance to moderate sub-zero temperatures in combination with its hybrid tea character and its *Rosa wichuraiana* ancestry. This variety with grafted bud and plant above that bud, entirely exposed above ground to moderate sub-zero temperatures survived and bloomed normally the following season. The word "temperature" herein refers to the Fahrenheit scale.

Comparisons: I know of no rose variety that so nearly resembles in form the bloom of the species known commercially as the *Ranunculus asiaticus* (not of genus Rosa), as my new rose.

In color my new rose is comparable with that of the new rose variety "Fashion" (Plant Patent 789). My rose is slightly deeper in color, and has many more petals, with a tendency to curl inward and usually not outward.

I claim:

The new and distinct variety of rose plant as described and illustrated, characterized by its form, its colors and color pattern, and its Wichuraiana traits.

JOSEPHINE D. BROWNELL.

REFERENCES CITED

The following references are of record in the file of this patent:

UNITED STATES PATENTS

| Number | Name | Date |
|---|---|---|
| Pl. Pt. 789 | Boerner | Mar. 16, 1948 |

OTHER REFERENCES

American Rose Annual, 1948, pp. 260, 261.

Bailey, "Standard Cyclopedia of Horticulture," vol. 3, pp. 2905–2909, 1943.